(12) United States Patent
Rotman

(10) Patent No.: US 11,076,577 B1
(45) Date of Patent: *Aug. 3, 2021

(54) HEALTH MONITORING CAT LITTER

(71) Applicant: Pretty Litter, Inc., Los Angeles, CA (US)

(72) Inventor: Daniel Joseph Rotman, Los Angeles, CA (US)

(73) Assignee: PRETTY LITTER, INC., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/870,659

(22) Filed: May 8, 2020

Related U.S. Application Data

(63) Continuation of application No. 15/229,901, filed on Aug. 5, 2016, now Pat. No. 10,660,301.

(Continued)

(51) Int. Cl.
| | |
|---|---|
| *A01K 1/015* | (2006.01) |
| *A01K 23/00* | (2006.01) |
| *A61B 5/00* | (2006.01) |
| *A61C 19/04* | (2006.01) |
| *G01N 33/74* | (2006.01) |

(Continued)

(52) U.S. Cl.
CPC .......... *A01K 1/0154* (2013.01); *A01K 1/0152* (2013.01); *A01K 1/0157* (2013.01); *A01K 23/005* (2013.01); *A61B 5/6802* (2013.01); *A61B 5/6808* (2013.01); *A61B 5/6817* (2013.01); *A61B 5/6887* (2013.01); *A61C 19/04* (2013.01); *G01N 21/78* (2013.01);

(Continued)

(58) Field of Classification Search
CPC ... A01K 1/0152; A01K 1/0154; A01K 1/0155
See application file for complete search history.

(56) References Cited

U.S. PATENT DOCUMENTS

| | | | | |
|---|---|---|---|---|
| 3,978,818 A | * | 9/1976 | Heldenbrand | ....... A01K 1/0107 119/170 |
| 5,108,897 A | * | 4/1992 | Steinetz | ................. G01N 33/74 435/7.9 |

(Continued)

FOREIGN PATENT DOCUMENTS

CN  107750974 A  3/2018

*Primary Examiner* — Michael H Wang
(74) *Attorney, Agent, or Firm* — Perkins Coie LLP; Colin Fowler

(57) ABSTRACT

Technology is disclosed for a cat litter that can be used to diagnose feline medical conditions. A cat litter contains an additive, e.g., a chemical agent, such as a natural and/or synthetic agent, that changes in color when it comes in contact with cat urine or feces. Based on the color it can be determined whether the cat has a medical condition, such as particular illness. For example, if the litter turns yellow when it comes in contact with the urine, it can indicate that the cat is healthy. If the litter turns to a color other than yellow, e.g., green, it can indicate that the cat has some illness. The cat then be taken to a veterinary doctor for further diagnosis. The chemical agent aids in detection and diagnosis through interaction of materials that change colors to indicate reactions with specific chemicals, cells, molecules, DNA and/or materials. The technology can be implemented for medical diagnosis and detection—for humans and/or animals.

19 Claims, 5 Drawing Sheets

Related U.S. Application Data

(60) Provisional application No. 62/202,591, filed on Aug. 7, 2015, provisional application No. 62/287,102, filed on Jan. 26, 2016.

(51) Int. Cl.
*G01N 33/68* (2006.01)
*G01N 21/78* (2006.01)

(52) U.S. Cl.
CPC ........... *G01N 33/689* (2013.01); *G01N 33/74* (2013.01); *A61B 2503/40* (2013.01); *G01N 2333/64* (2013.01)

(56) References Cited

U.S. PATENT DOCUMENTS

| | | | | |
|---|---|---|---|---|
| 5,143,023 A * | 9/1992 | Kuhns | ................. | A01K 1/0152 119/171 |
| 5,267,532 A * | 12/1993 | Franklin | .............. | A01K 1/0152 119/171 |
| 5,359,960 A * | 11/1994 | Yananton | ............. | A01K 1/0107 119/165 |
| 5,371,054 A * | 12/1994 | Pluta | .................... | A01K 1/0152 119/173 |
| 5,685,259 A * | 11/1997 | Santioemmo | ........ | A01K 1/0125 119/168 |
| 5,830,765 A * | 11/1998 | Santioemmo | ........ | A01K 1/0125 436/66 |
| 6,019,062 A * | 2/2000 | Lombard | ............. | A01K 1/0152 119/172 |
| 6,162,646 A * | 12/2000 | Webster | ................. | G01N 21/80 422/420 |
| 6,267,722 B1 * | 7/2001 | Anderson | .......... | G01N 21/8483 600/300 |
| 6,308,658 B1 * | 10/2001 | Steckel | ................ | A01K 1/0152 119/171 |
| 6,382,132 B1 * | 5/2002 | Steckel | ................ | A01K 1/0152 119/171 |
| 7,485,466 B2 * | 2/2009 | Jenkins | .............. | G01N 33/6803 119/173 |
| 7,533,630 B2 * | 5/2009 | Steckel | ................ | A01K 1/0152 119/165 |
| 7,670,845 B2 * | 3/2010 | Wenzel | ................ | A01K 1/0152 436/163 |
| 7,951,547 B2 * | 5/2011 | Elsemore | ........... | G01N 33/5308 435/7.1 |
| 8,062,902 B2 * | 11/2011 | Mestrallet | ............ | A01K 1/0152 436/169 |
| 8,268,574 B2 * | 9/2012 | Elsemore | .............. | C07K 16/00 435/7.22 |
| 9,144,224 B2 * | 9/2015 | Goff | ........................ | B01J 20/24 |
| 9,283,540 B2 * | 3/2016 | Fritter | .................. | A01K 1/0154 |
| 9,675,503 B2 | 6/2017 | Carney | | |
| 9,795,112 B2 * | 10/2017 | Goff | .................... | A01K 1/0155 |
| 2003/0170905 A1 * | 9/2003 | Kamyshny | ........... | A01K 1/0152 436/164 |
| 2010/0307422 A1 * | 12/2010 | Huck | .................. | A01K 1/0152 119/161 |
| 2016/0205889 A1 | 7/2016 | Bin | | |

* cited by examiner

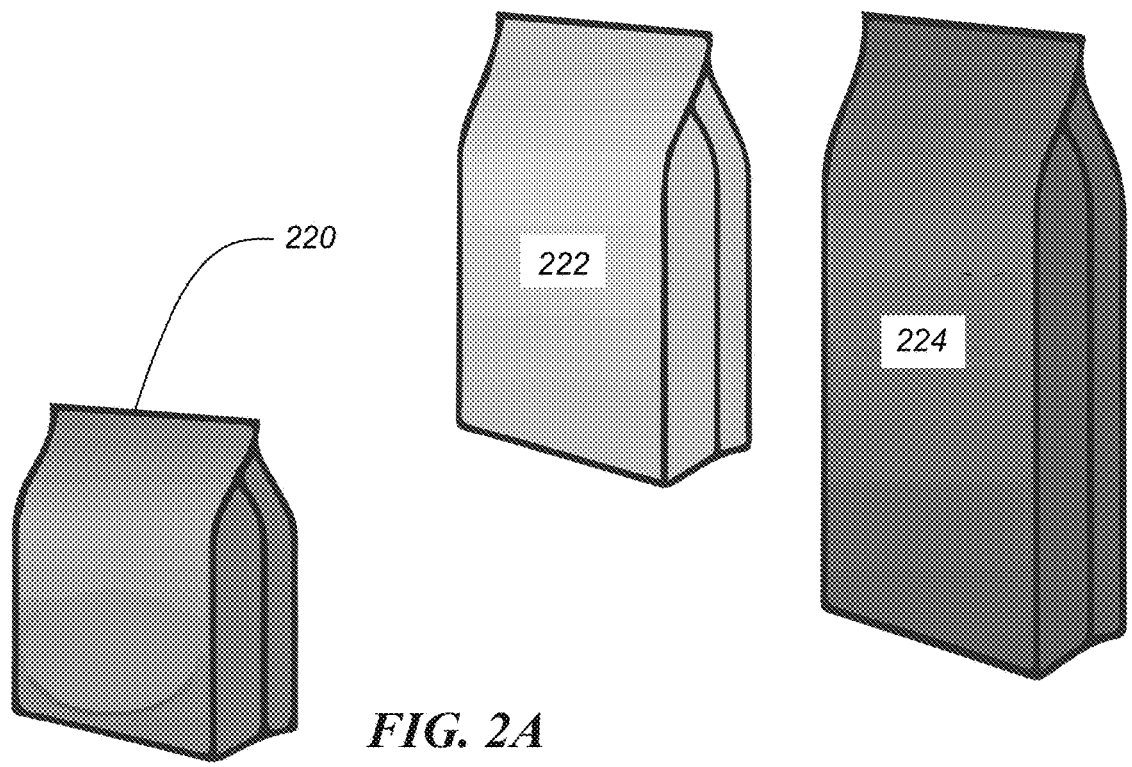
*FIG. 2A*
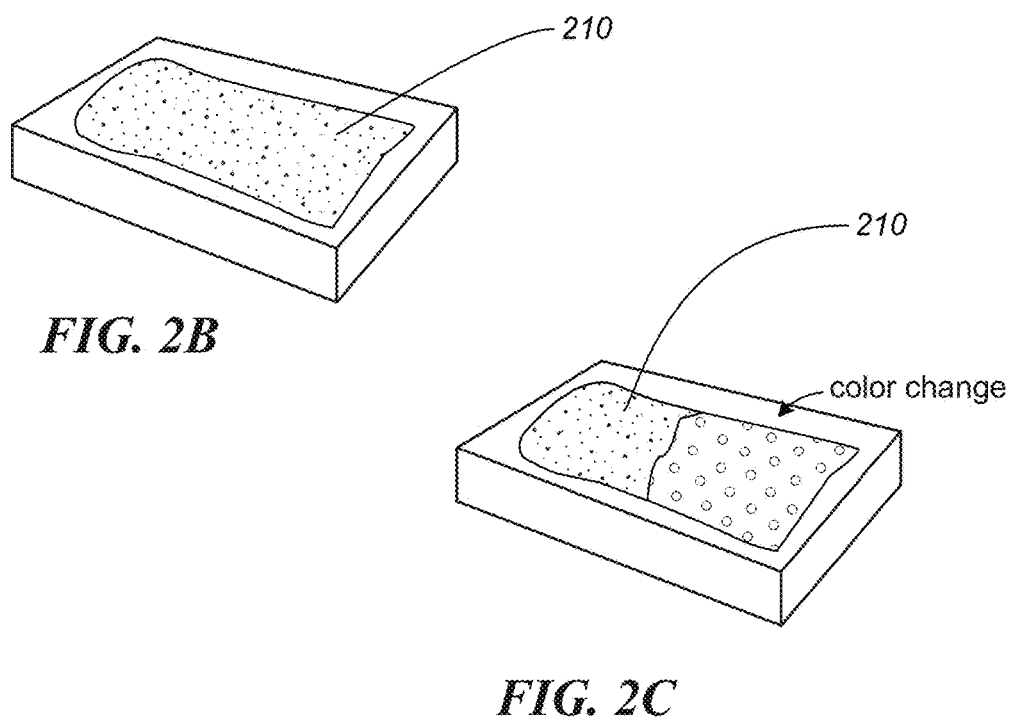
*FIG. 2B*
*FIG. 2C*

HEALTH MONITORING CAT LITTER

CROSS-REFERENCE TO RELATED APPLICATIONS

The present application is a continuation application of U.S. patent application Ser. No. 15/229,901, filed Aug. 5, 2016, which claims priority to U.S. Provisional Patent Application No. 62/202,591, filed Aug. 7, 2015, and U.S. Provisional Patent Application No. 62/287,102, filed Jan. 26, 2016, the disclosures of which are both incorporated herein by reference in their entireties.

TECHNICAL FIELD

Several of the disclosed embodiments relate to health monitoring using sensory technology and materials science, and more specifically, to a color-changing cat litter that facilitates identifying specific feline medical conditions, such as for detection and eventual diagnosis.

BACKGROUND

Current litter use color changing pH strips to test for urinary anomalies. Some litters use additives that are mixed into compositions in order to add the ability to change color for detecting glucose levels. However, the testing capabilities of the current litter are limited. For example, current cat litters are restricted to facilitating testing of Feline Urinary Tract Disorder or Feline Diabetes in urine. They also do not facilitate testing of feces. In addition, they do not facilitate testing for illnesses that can be passed on to humans, such as toxoplasmosis, which affects children, pregnant women and people with weak immune systems. Furthermore, these methods use cost-prohibitive materials not conducive to mass production, produce too many false-positives and false-negatives and some of these methods have expiration dates on their product.

SUMMARY

Embodiments are disclosed for a sensory technology and material science that aids in detection and diagnosis through interaction of materials that change colors to indicate reactions with specific chemicals, cells, molecules, DNA, components and/or materials. The technology can be implemented for various purposes, e.g., medical diagnosis—for humans and/or animals. In some embodiments, the technology can be implemented in a cat litter for diagnosing feline illnesses and other medical conditions. A cat litter contains one or more additives or materials, e.g., natural and/or synthetic, that changes in colors when it comes in contact with cat urine or feces. Based on the color it can be determined whether the cat has any illness or other medical condition. For example, the cat litter can be white in color. If the litter turns yellow when it comes in contact with the urine, it can indicate that the cat is healthy. However, if the litter turns to a color other than yellow, e.g., green, orange, it can indicate that the cat has some illness. The cat can then be taken to a veterinary doctor for further diagnosis. In some embodiments, the litter changes the color due to existence or non-existence of one or more constituents in cat excreta.

BRIEF DESCRIPTION OF THE DRAWINGS

FIGS. 2A-2C are examples illustrating advantages and use of a cat litter in accordance with various embodiments.

DETAILED DESCRIPTION

Embodiments are disclosed for a sensory technology and material science that aids in detection and diagnosis through interaction of materials that change colors to indicate reactions with specific chemicals, cells, molecules, DNA, components and/or materials. The technology can be implemented for various purposes, e.g., medical diagnosis—for humans and/or animals. In some embodiments, the sensory technology can be used to create one or more chemical agents that can be placed on and mixed with a variety of different materials, both synthetic and natural, that when interacting with another chemical compound, e.g., a chemical compound that is being tested, can change in to a specific color. This change in color can be used to detect a specified characteristic of the chemical compound being tested. In some embodiments, the change in color can be due to an existence or non-existence of a set of constituents in the chemical compound corresponding to a medical condition.

In some embodiments, the technology can be implemented in a cat litter for monitoring and/or diagnosing feline illnesses and other medical conditions. A cat litter contains one or more additives, e.g., natural and/or synthetic, that change in colors when they come in contact with cat urine or feces. In some embodiments, the litter, e.g., available in the market, can be mixed with a chemical agent made using the sensory technology which changes in color when it encounters diseases, illnesses, and/or other medical conditions in the urine or feces of a mammal, such as a cat. Based on the color it can be determined whether the cat has any medical conditions. For example, the cat litter can be white in color. If the litter turns yellow when it comes in contact with the urine or feces, it can indicate that the cat is healthy. However, if the litter turns to a color other than yellow, e.g., green, orange, it can indicate that the cat has some illness, while another color, e.g., red, dark pink, purple, can indicate that the cat has a medical condition other than an illness, such as pregnancy. The cat can then be taken to a veterinary doctor for further diagnosis. In some embodiments, the chemical agent mixed with the litter is made such that it turns to the color of the urine if the cat does not have any illness or other medical condition.

Figure 1A:
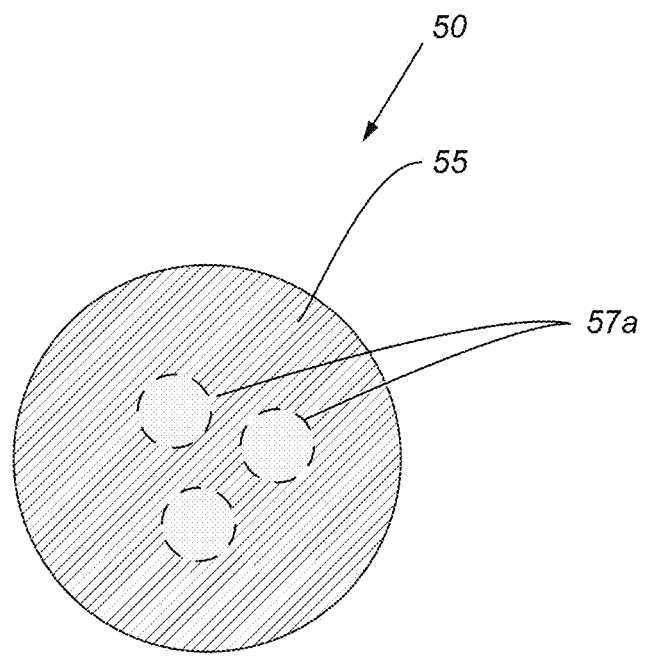
FIGS. 1A and 1B are examples showing individual particles of a cat litter in accordance with various embodiments.

FIG. 1A shows an example particle 50 of a plurality of like particles (not shown) that can form a cat litter in accordance with an embodiment of the present technology. As shown, the particle 50 includes a base material 55 and one or more first additives 57*a* that are combined with the base material 55. In some embodiments, the base material 55 can include porous silica (e.g., a clear or transparent silica gel) having large pore diameters (e.g., 400 Å; although larger or smaller pore diameters are contemplated), and the additives 57*a* can be substantially or completely held within the pores (e.g., via surface interactions within the pores). In certain embodiments, the base material 55 can include a silica gel and certain additives disclosed in U.S. Pat. No.

8,062,902, which is incorporated by reference by herein in its entirety. Such silica gel can have a particle size in the range of, e.g., 0.5 mm to 2 mm, 0.5 to 5.0 mm, 0.5 to 6.0 mm. In some embodiments, the base material 55 can include other suitable porous base materials having a pore size selected such that pores can substantially contain the one or more first additives 57a partially or completely within the base material. The additives can include, for example, Bromothymol Blue to detect pH; (2) Diisopropylbenzene Dihydroperoxide to detect Blood; (3) Tetrabromophenol Blue to detect Protein; and (4) Glucose Oxidase to detect Glucose. In addition or alternately, the additives 57a can include other additives, as described below.

In use, the first additives 57a can react with constituents in cat excreta, including urine and fecal material. In some embodiments, the pore size of the base material 55 can be selected such that the urine can at least partially evaporate from the particle 50 through the pores over time, yet still reside within the pore for sufficient time so as to facilitate chemical interactions between the constituents in the urine and the first additives 57a before complete or substantial evaporation.

Figure 1B:
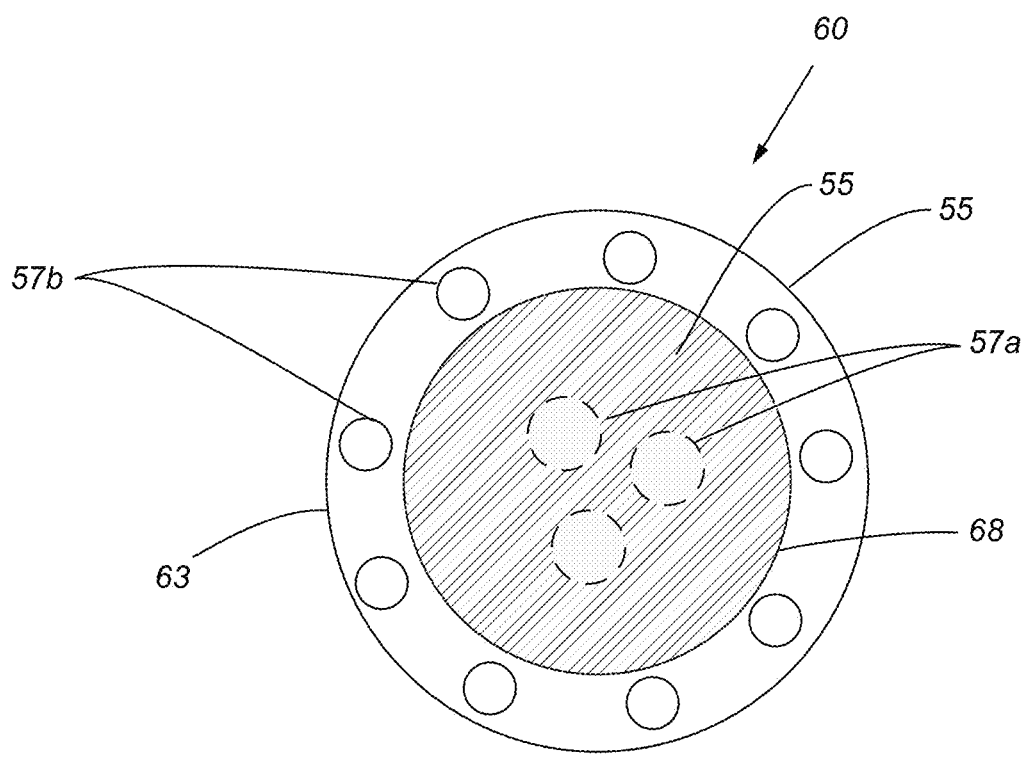

FIG. 1B shows an example of another particle of a plurality of like particles (not shown) that can form a cat litter in accordance with an embodiment of the present technology. The particle can be similar in some aspects to the particle 50 described above with reference to FIG. 1A. However, the particle 60 further includes one or more second additives 57b formed substantially over an exterior surface 68 of the base material 55. In some embodiments, the second additives 57b can be held to the surface 68 via surface interactions with the exterior surface and/or areas of the pores (not shown) adjacent the exterior surface. In some embodiments, a coating or membrane 62 (e.g., a cellulose or other suitable membrane or spray coating) can facilitate binding of the second additives 57b to the base material 55.

In some embodiments, the first and second additives 57a and 57b can both react with constituents in cat excreta. For example, in certain embodiments the second additives 57b can detect a first type medical condition (e.g., a first type of illness) with a corresponding color change, as further described below. The first additives 57a can detect a different type of medical condition (e.g., a second type of illness), as described below. In these and other embodiments, the membrane 62 can be configured to have a selected porosity to allow for the flow of fluid (e.g., urine) therethrough so as to allow for interaction between the constituents in the urine and the first additives 57a. Further, the membrane 62 can dissolve in the presence of certain analytes.

In certain embodiments, the particle 60 can be configured to perform a discrete (e.g., micro-scale) flow assay, akin to a lateral flow assay. For example, the second additives 57b can include color particles (e.g., nano- or micro-particles) that are conjugated for a target analyte, and the first additives 57a can include an anti-target analyte configured to capture conjugated color particles. In some embodiments, the target analyte can be Relaxin, which can be indicative of pregnancy in felines. See "Pregnancy Diagnosis in Cats Using a Rapid, Bench-top Kit to Detect Relaxin in Urine," *Reproduction in Domestic Animals*, Volume 42, Issue 1, pgs. 111-112, February 2007, which is incorporated herein by reference in its entirety. Without being bound by theory, it is believed that in certain cases repeated exposure to urine and evaporation thereof over an extended time period (e.g., several days or weeks) could provide sufficient time for a detectable interaction with Relaxin in urine and the additives 57a and 57b. In addition to or in lieu of detecting Relaxin in Urine, Relaxin can also be detected in blood. The second additives 57b can include, for example, colloidal gold nanoparticles and latex microspheres, which may be configured to appear as, e.g., red, dark pink, purple, blue, or other colors when a target analyte is detected. In some of these embodiments, the particle 60 can include a material membrane that is configured to dissolve to facilitate release of the conjugated nano- or micro-particles for adsorption into the pores of the base material 55 when exposed to urine.

In various embodiments, the cat litter can be a mixture with a certain concentration by weight of the particles 50 and 60. For example, in some embodiments, the mixture of each of particle types can be 50/50, while in other embodiments, the cat litter can include a greater concentration (up to 100% concentration) of the former particle type or a lesser concentration (e.g., 0%). In additional or alternate embodiments, the cat litter can include a mixture of different types of the particle 50 shown in FIG. 1A with certain particles having one type of additive to detect the presence or absence of certain constituents and another particle with a different type of additive to detect the presence or absence of other types of constituents.

In use, the cat litter can help the cat owners in taking care of their cats' health by testing for medical conditions, such as illnesses, in both urine and feces. The cat litter can indicate various illnesses (examples of which are described below), including toxoplasmosis, and illness that can affect humans too. The cat litter uses cost-effective materials. In some embodiments, the margin for false-positives and false-negatives is none to minimum.

In one aspect of the technology, the cat litter can absorb liquid and/or odor, e.g., of the cat waste, within a specified period from the time the litter comes in contact with the cat waste. In some embodiments, the chemical agents in the cat litter are made such that the liquid and odor are absorbed almost instantaneously. Further, the cat litter is made such that the liquid evaporates from the litter and the odor is still locked in.

Some of the elements that the cat litter test for include, but not limited to:
Urinary Elements
    Urine Specific Gravity: If <1.020—low USG can indicate a potential kidney disease (66% loss of renal function) or endocrine disorders affecting the urine concentrating ability of the kidney
    Glucose: Diabetes Mellitus
    Bilirubin: Liver disease, cholestasis, hemolysis
    White Blood Cells: kidney/bladder infection/inflammation
    Red Blood Cells: kidney/bladder infection/inflammation
    Crystals: Struvite/CaOx, crystaluria (crystals in urine) detection
    Protein: renal disease, hypertension, amyloidosis, etc.
    Ketones: ketoacidosis
    pH detection: Urinary anomalies or related illnesses
Feces Elements, e.g., that relate to parasitism:
    Toxoplasmosis
    Round worms
    Hook worms
    Tape worms
    Giardia
    *Cryptosporidium*

FIGS. 2A-2C are pictorial examples illustrating advantages and use of a cat litter 210 made using, e.g., the particles 50 (FIG. 1A) and/or the particles 60 (FIG. 1B) in accordance with various embodiments. Referring to FIGS. 2A and 2B together, the cat litter 210 (FIG. 2B) can poured into a tray from a bag 220 (FIG. 2A) containing the litter. The litter 210 is then uniformly spread out, as shown in FIG. 2B, and ready for use by the cat. The cat litter 210 is monitored, e.g., according to a specified frequency, to check the color of the litter after the cat. If the color of the portion of the litter that is in contact with the cat waste is the same color as the urine, then the cat is normal. If the color of the litter is different from that of the urine (as shown in FIG. 2C), then the cat may have some illness or other medical condition.

The cat waste is removed from the litter 210 and the litter can be mixed thoroughly to avoid saturating the same point, e.g., the point from which the waste is removed. After a specified period, e.g., a month, the litter can be removed and the tray be filled with new litter.

Referring to FIG. 2A, the cat litter 220 is made using a light-weight formula that enables minimizing the consumption of the cat litter. That is, a specified quantity of the pretty litter can be used for a longer period than other traditional cat litters 222 and 224. In some embodiments, the cat litter 210 can be made by mixing a cat litter that is generally available in the market with one or more chemical agents, e.g., made using the sensory technology, that changes in color when it comes in contact with the cat urine or feces. In some embodiments, the pretty litter can be made by manufacturing the cat litter with the one or more chemical agents.

Figure 3:
FIG. 3 is a pictorial of an example illustrating a color change in the cat litter indicating an illness, in accordance with various embodiments.

FIG. 3 is a pictorial of an example 300 illustrating a color change in the cat litter indicating an illness, consistent with various embodiments. In the example 300, the portion of the litter that is contact with the cat urine has turned into a blue color, which can indicate an illness. As described earlier, if the color is same color as the urine, then the cat is normal and if it is different than that of the urine, the cat can have a medical condition, such as an illness. Although the examples illustrate that a yellow color (e.g., urine color) indicates healthy urine and other colors indicate an illness in the cat, the above colors are just illustrative and various other colors can be used to indicate normal or abnormal conditions. Further, the color of the litter, e.g., unused litter, can also be any of a variety of colors.

Figure 4:
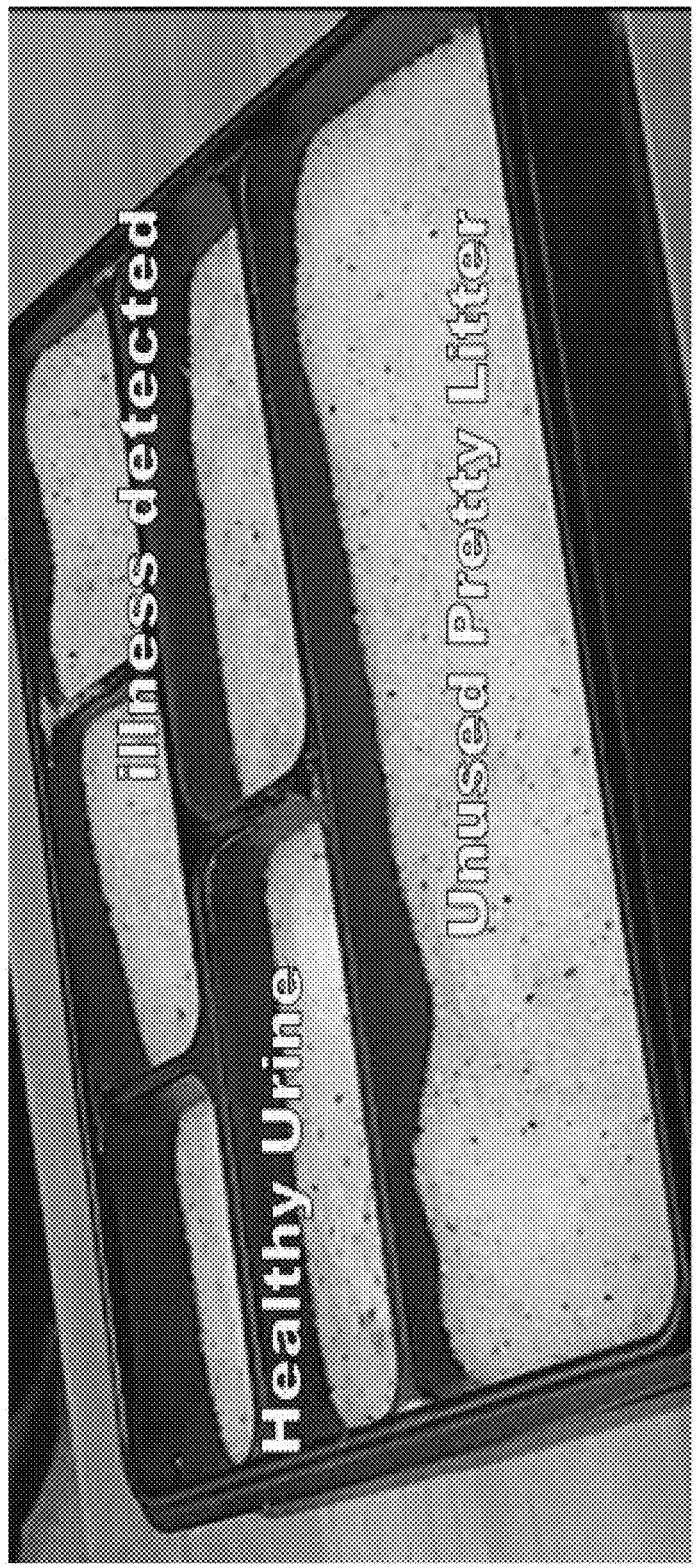
FIG. 4 is a pictorial of an example illustrating a cat litter that has turned into various colors indicating various illnesses, in accordance with various embodiments.

FIG. 4 is a pictorial of an example 400 illustrating a cat litter that has turned into various colors indicating various illnesses, consistent with various embodiments. In the example 400, the portion of the litter marked "unused" indicates the litter that is unused. Note that the unused litter in this example 500 is white in color. The portion of the litter with a yellow spot, e.g., marked "healthy urine," indicates healthy urine. The portion of the litter with green and orange spots, e.g., marked "illness detected," indicates that the urine is abnormal and that the cat has some illness. As described earlier, the above colors are just illustrative and various other colors can be used to indicate normal or abnormal conditions.

Figure 5:
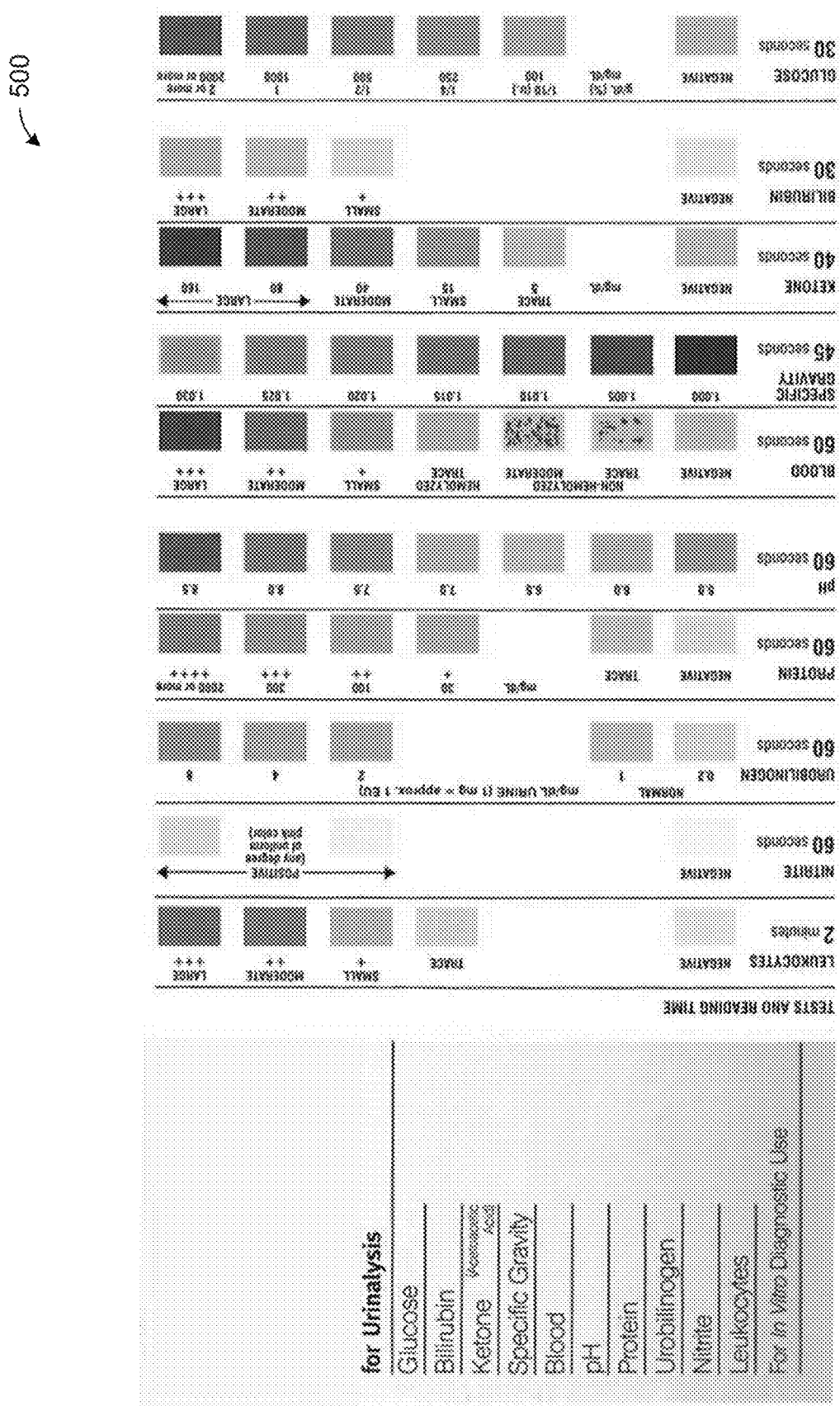
FIG. 5 is an example illustrating a significance of various colors that may occur in a chemical agent when in contact with a cat waste, in accordance with various embodiments.

FIG. 5 is an example 500 illustrating a significance of various colors that may occur in a chemical agent when in contact with a cat waste, consistent with various embodiments. The example 500 illustrates the various possible colors that might occur in a urine analysis dipstick, which includes chemical agents made using the sensory technology, when dipped into the cat urine. For example, an orange color can indicate that the urine has a pH of 5.0. In some embodiments, different tests have different read times, e.g., the dipstick has to be dipped for different periods for getting readings of different parameters.

The technology can be implemented in various forms other than the litter, and for both humans and animals. The materials used in this technology can efficiently, accurately and easily test for specific circumstances in both humans and animals in a painless and cost-efficient manner. The chemical agents prepared using the sensory technology can be used with various equipment, instruments, liquids, apparatus for detecting and diagnosing characteristics of chemical compounds in various forms. The chemical agents can be made using a variety of formulae, processes, technologies, e.g., sensory technology, and from natural and/or synthetic materials.

The embodiments can include a chemical formula utilizing sensory technology of both natural and synthetic materials that is able to change colors when testing for the existence of any organic or synthetic material and its components.

The embodiments can include a cat litter that can detect feline illnesses in waste by changing colors.

The embodiments can include a synthetic material that can change color when detecting specific chemicals, cells, molecules, DNA, components and/or materials. For example, a plastic bag that changes color when it detects illness in a dog's waste.

The embodiments can include an absorbent pad that changes colors when it detects illness in a mammal's waste. For example, a dog pee pad.

The embodiments can include a synthetic material that can be worn and changes color when detecting an illness. For example, a diaper that changes color when detecting illness in a person's urine or feces.

The embodiments can include a synthetic or natural material than can be worn and changes color when detecting sexually transmitted diseases. For example a color changing condom when in contact with an STD.

The embodiments can include a synthetic or natural material that can be used as a wipe against the body of a mammal to detect abnormalities or illnesses and change color as a result. For example, a wipe to respond to secondary infection in canines such as *Malassezia* or verify the presence of fleas.

The embodiments can include a liquid that changes color when detecting specific chemicals, cells, molecules, DNA, components and/or materials. For example, a skin lotion that changes color when it detects basal cell carcinoma, squamous cell cancers and/or melanoma. Or an additive to toilet water to detect anomalies or illnesses in human urine.

The embodiments can include an instrument that can be inserted into the ear of a mammal to test for sickness, illness or abnormalities by changing colors if detected. For example, a swap for canines to detect *Pseudomonas otitis* in the ear.

The embodiments can include a compound that can be added to a strip and placed against the gums of a mammal that changes color of any disease is detected. For example, a test strip is rubbed along the gum line and within a short amount of time the strip changes color if thiol levels are present, indicating disease activity such as gingivitis or periodontitis.

Embodiments can further include one or more medical diagnostic tool disclosed in U.S. Provisional Application No. 62/287,102, the entirety of which is incorporated by reference, as noted above

REMARKS

The above description and drawings are illustrative and are not to be construed as limiting. Numerous specific details are described to provide a thorough understanding of the disclosure. However, in certain instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Those skilled in the art will appreciate that the logic illustrated in each of the flow diagrams discussed above, may be altered in various ways. For example, the order of the logic may be rearranged, substeps may be performed in parallel, illustrated logic may be omitted; other logic may be included, etc.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

I claim:

1. A pet litter, comprising a plurality of health monitoring particles, each of the health monitoring particles consisting essentially of:
a porous base material; and
a plurality of additives applied via a spray coating to the porous base material, the plurality of additives including a first additive and a second additive are configured to cause a change in color of the pet litter when coming in contact with pet excreta, and wherein the change in color is indicative of the existence or non-existence of at least one medical condition in an associated pet, wherein the first additive is contained within pores of the porous base material and is configured to detect a pH level and the second additive is positioned on the exterior surface of the porous base material and is configured to react with a target analyte.

2. The pet litter of claim 1 wherein the plurality of additives include a first additive and a second additive, and wherein both of the first additive and the second additive changing in color indicates at least two medical conditions exist in the associated pet.

3. The pet litter of claim 1, wherein the porous base material comprises amorphous silica.

4. The pet litter of claim 1 wherein the at least one medical condition includes at least one of illness and pregnancy.

5. The pet litter of claim 1 wherein the plurality of additives further includes a third additive forming a coating or membrane that encases the first and second additives and the porous base material.

6. The pet litter of claim 5 wherein the porous base material is substantially neutral in pH.

7. The pet litter of claim 1 wherein both the first and second additives are configured to react with the pet excreta.

8. The pet litter of claim 7 wherein:
the first additive includes color particles conjugated to a target analyte; and
the second additive includes an anti-target analyte configured to capture the conjugated color particle.

9. The pet litter of claim 8 wherein:
the medical condition includes pregnancy; and
the target analyte is Relaxin.

10. The pet litter of claim 9 wherein the color particles are colloidal gold nanoparticles.

11. The pet litter of claim 9 wherein the color particles are latex microspheres.

12. The pet litter of claim 1 wherein the plurality of additives are configured to turn into a first color indicating a first condition of the pet excreta.

13. The pet litter of claim 12, wherein the first condition indicates an existence or non-existence of a set of constituents in the pet excreta that is observed in a healthy cat.

14. The pet litter of claim 12, wherein the plurality of additives include chemical agents that cause the pet litter to turn into a second color indicating a second condition of the pet excreta.

15. The pet litter of claim 14, wherein the second condition indicates an existence or non-existence of a set of constituents in the pet excreta that is observed in a pet that is having an illness.

16. A method of fabricating the pet litter of claim 1, comprising:
spray coating the porous base material with a plurality of additives.

17. A pet litter comprising:
a porous base material; and
a plurality of reactive dyes that are applied via a spray coating technique and are positioned both on and within the porous base material, wherein a first reactive dye is contained within pores of the porous base material and a second reactive dye is applied as a membrane on an exterior of the porous base material, and wherein the first reactive dye causes a first change in color of the pet litter when contacting with pet urine including constituents indicative of a first medical condition and the second reactive dye causes a second change in color of the pet litter when contacting with pet fecal matter including constituents indicative of a second medical condition.

18. The pet litter of claim 17 wherein the porous base material comprises amorphous silica.

19. The pet litter of claim 17,
the first reactive dye includes color particles conjugated to a target analyte; and
the second reactive dye includes an anti-target analyte configured to capture the conjugated color particle.

* * * * *